United States Patent [19]

Wessels

[11] Patent Number: 4,926,857
[45] Date of Patent: May 22, 1990

[54] DEVICE FOR TREATING LIFE FORMS WITH TWO DIFFERENT TYPES OF FOCUSED ACOUSTICAL WAVES

[75] Inventor: Gerd Wessels, Erlangen, Fed. Rep. of Germany

[73] Assignee: Siemens Aktiengesellschaft, Berlin and Munich, Fed. Rep. of Germany

[21] Appl. No.: 156,240

[22] Filed: Feb. 16, 1988

[30] Foreign Application Priority Data

Feb. 16, 1987 [DE] Fed. Rep. of Germany .... 3704836.8

[51] Int. Cl.$^5$ .............................................. A61B 17/22
[52] U.S. Cl. .................. 128/24 A; 128/804; 606/128
[58] Field of Search ................ 128/660.03, 24 A, 804, 128/328; 606/127, 128

[56] References Cited

U.S. PATENT DOCUMENTS

| | | | |
|---|---|---|---|
| 3,338,235 | 8/1967 | Gordon | 128/660.03 |
| 3,499,437 | 3/1970 | Balamuth | 128/24 A |
| 4,484,569 | 11/1984 | Driller et al. | 128/660.03 |
| 4,586,512 | 5/1986 | Do-Huu et al. | 128/660.03 |
| 4,620,546 | 11/1986 | Aida et al. | 128/660.03 |
| 4,658,828 | 4/1987 | Dory | 128/660.03 |

Primary Examiner—Ruth S. Smith
Attorney, Agent, or Firm—Hill, Van Santen, Steadman & Simpson

[57] ABSTRACT

A sound generator for treating life forms with focused acoustical waves, characterized by an electrical drivable sound source, focusing arrangement for the acoustical waves coming from the sound source and an electrical generator arrangement for driving the sound source. The generator arrangement includes at least two different generators, which are connectible to the sound source by a switch arrangement and which will drive the sound source for generating different types of acoustical waves, for example shock waves and a continuous sound or acoustical wave. The sound source may be composed of a single transducer or a plurality of transducers.

16 Claims, 1 Drawing Sheet

DEVICE FOR TREATING LIFE FORMS WITH TWO DIFFERENT TYPES OF FOCUSED ACOUSTICAL WAVES

BACKGROUND OF THE INVENTION

The present invention is directed to a sound or acoustical waves generator or device for treating a life form with focused acoustic waves. The device includes an electrical, drivable sound source, focusing means for focusing acoustical waves created by the sound source and an electrical generator means for driving the sound source.

Sound generators or devices, which usually emit acoustical waves in an ultrasonic region, are employed, for example, in the treatment of pathological tissue changes, for example, tumors. The sound generator emits acoustical waves, which are suitably fashioned for a respective type of treatment, and they are essentially continuous sound.

A sound generator which is used for cell destruction is disclosed in U.S. Pat. No. 4,315,514, whose disclosure is incorporated by reference. A radio-frequency generator is provided as the generator means, which supplies a periodic AC voltage of a suitable frequency to the sound source.

It has been shown that better success is achieved in the treatment of pathological tissue change when the tissue zones to be treated are also charged with differently constituted acoustical waves, for example shock waves, in addition to being charged with continuous sound or acoustical waves. A lasting disturbance of the metabolism of the cell, which can result in their mortality, can be achieved by this method.

Systems, which have a sound generator which emits acoustical waves, namely shock waves, that deviate from a continuous sound, are known and an example is disclosed in German Published Application No. 33 19 871. This sound generator, however, is provided for non-contacting disintegration of calculi in the body of the patient and is unsuitable for the treatment of pathological tissue changes.

Even if this last mentioned sound generator were adapted to the requirements for treatment of tissue, two sound generators would be required for treating pathological tissue changes with both a continuous wave and a shock wave, since the known sound generators can, respectively, output only one type of acoustical wave. This is complicated and stands in the way of the introduction of the type of treatment in practice.

SUMMARY OF THE INVENTION

The object of the present invention is to construct a sound generator or device for focusing acoustical waves for the treatment of a life form that can output different types of acoustical waves.

This object is achieved in an improvement in a sound generating system for treating life forms with focused acoustical waves comprising an electrically drivable sound means for creating acoustical waves for treating a life form, means for focusing the acoustical waves coming from the sound means, and electrical generator means for driving the sound means. The improvement comprises the generator means having at least two generators and switch means for selectively connecting the two generators to the sound means to drive the sound means for generating different acoustical waves for treating the life form.

With the sound generator of the invention, thus, the tissue zone to be treated can be charged with differently fashioned acoustical waves. In accordance with the modification of the invention, it can therefore be provided that the sound source is selectively connectible to one of the generators. The sound source, however, can also be composed of at least two acoustical transducers, which are drivable independent of one another, and each is respectively connected to the generator. There is, then, the possibility of optimally adapting the acoustical transducer to the respective type of acoustical wave to be emitted. Moreover, there is also the possibility in this case of simultaneously driving a plurality of acoustical transducers with the respective generator so that the plurality of types of acoustical waves can simultaneously act on the tissue zone to be treated.

In order to be able to emit the two most important types of acoustical waves required for the treatment of pathological tissue changes, the generator means, in a modification of the invention, comprises a generator for generating shock waves and a generator for generating continuous sound or acoustical waves. It can thereby be provided that the generator for generating continuous sounds can be intermittently operated to provide pulses or short periods of continuous acoustical waves. The possibility then exists of exploiting the time interval between the emissions of continuous sound for the purpose of undertaking a location of the region in the inside of the body to be treated with the assistance of echoes of the acoustical wave output by the sound generator. When emitting shock waves, there is also the possibility of utilizing the time interval between two successive shock waves for locating. The locating is possible in an especially simple way when, in accordance with the embodiment of the invention, the sound source is formed by at least one piezo-electric transducer, since this can emit not only the acoustical waves, but can also receive their echoes with adequate sensitivity.

When a piezo-electric transducer is employed as the sound source, it is provided in the modification of the invention that the piezo-electric transducer is connectible to a generator emitting high voltage pulses for generating shock waves and is also connected to a generator supplying a periodic or, respectively, intermittently periodic, AC voltage for generating continuous sound or, respectively, intermittent periods of continuous sound acoustical waves.

Other advantages and features of the present invention will be readily apparent from the following description of the preferred embodiments, the drawings and claims.

DESCRIPTION OF THE PREFERRED EMBODIMENTS

Figure 1:
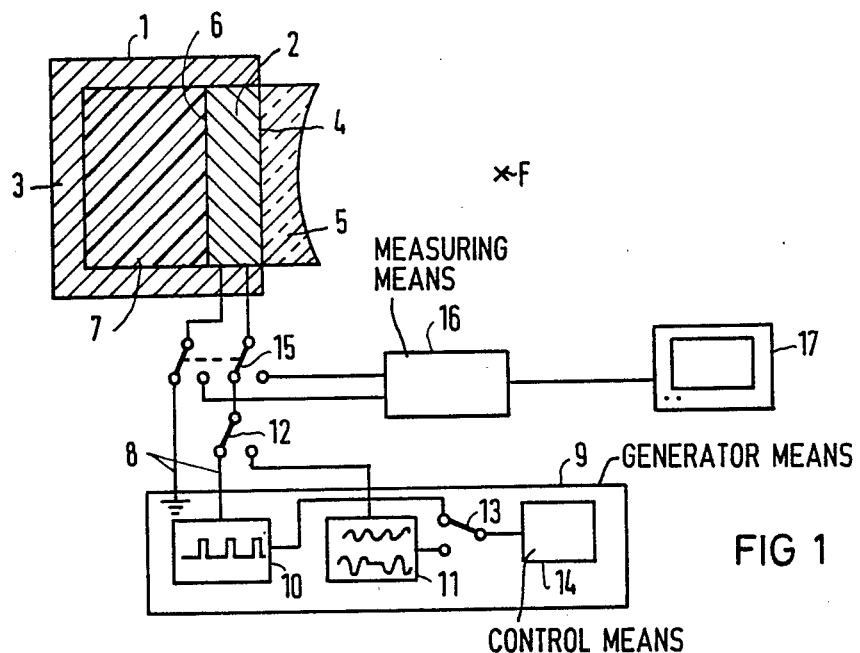
FIG. 1 is a schematic cross sectional view of a transducer connected to a generator means and also a locating means.

The principles of the present invention are particularly useful when incorporated in a sound generator system having a piezo-electric transducer 2, which is constructed wafer-like and/is arranged in a pot-like housing 1 as an electrically drivable sound means. As illustrated, the piezo-electric transducer 2 has a front or first end face 4 and a rear or second end face 6. The transducer 2 is located in a pot-like housing 1 with the front end face 4 directed away from a rear or base 3 of the housing. An acoustical lens 5, for focusing the emitted acoustical waves, is connected to the first or front end face 4 and will focus the waves to a focal point F. The housing 1 contains a dampening member 7 for dampening acoustical waves coming from the second or back surface 6, which is opposite the front surface 4.

The piezo-electric transducer is connected to a generator means 9 by two leads or lines 8. The generator means 9 have two generators 10 and 11 to which the piezo-electric transducer is selectively connectible via a switch means 12. When it is connected to the generator 10, the piezo-electric transducer 2 will receive high-voltage pulses schematically indicated in FIG. 1 for generating shock waves. When, by contrast, the piezo-electric transducer 2 is connected to the generator 11, it receives a periodic AC voltage, schematically shown in FIG. 1, for generating a continuous sound or acoustical wave.

The generator 10 is connected to a control means 14 by a switch means 13 in a first position (as illustrated). When the switch 13 is shifted to a second position, the generator 10 is disconnected from the control means 14 and the generator 11 is driven by the control means 14 so that its output has intermittent periods or pulses of periodic AC voltage, schematically shown in FIG. 1, and is applied to the piezo-electric transducer 2 for generating intermittent periods or pulses of continuous sound or acoustical wave instead of a continuous sound or acoustical wave.

A switch means 15 is provided in the lines 8 between the generator means 9 and the piezo-electric transducer 2. The piezo-electric transducer 2 is then optionally connected to a measuring means 16, which is connected to a viewing means or screen 17 instead of being connected to the generator means 9 by this switch 15. There is, then, the possibility of imaging the tissue zone situated in the region of the focal point F on the viewing means 17 from the echoes of the acoustical waves received by the transducer 2. To this end, the switch means 15 is connected to the control means 14 or, respectively, to the generator 10 in a way not illustrated, and is controlled so that when the outputting shock wave or the respective intermittent pulse of continuous sound is to be created, the piezo-electric transducer is connected to the generator means 9 during the emission of the shock wave or, respectively, continuous sound, and then is connected to the measuring means 16 in a time interval lying between the two pulses or periods from the generator means 9. This is a known way of pulsing and then receiving an echo pulse.

Figure 2:
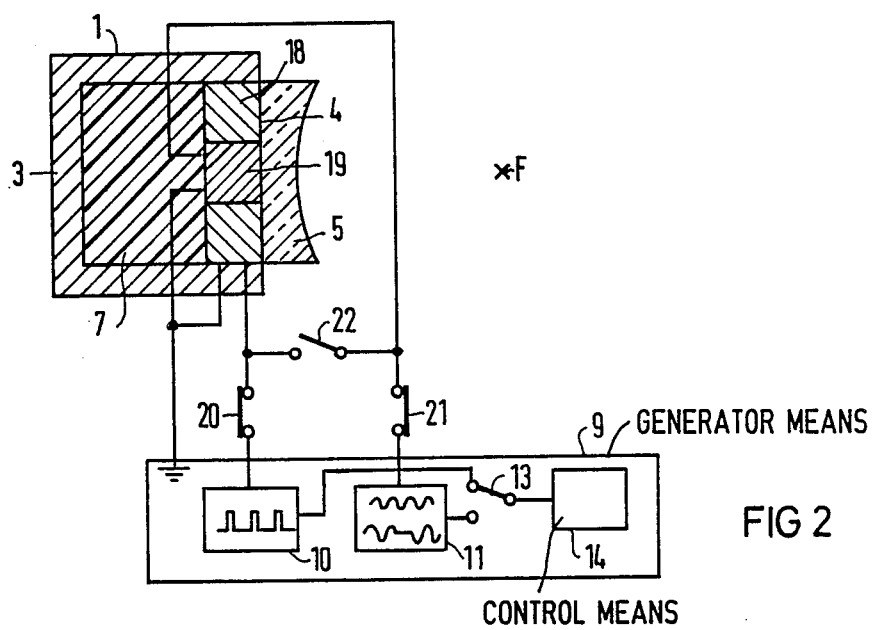
FIG. 2 is a schematic cross sectional view of an embodiment of the sound generator connected to a generator device.

An embodiment of the sound generator or device is shown in FIG. 2 and the means for locating the tissue zone to be treated are not illustrated. The second embodiment essentially corresponds to the arrangement of FIG. 1, for which reason identical parts are provided with the same reference characters. The essential difference of the embodiment of FIG. 2 over the device or sound system of FIG. 1 is that the sound source is composed of two piezo-electric transducers 18 and 19, which are independent of one another. The transducer 18 is connected to the generator 10 by a switch means 20 and the transducer 19 is connected to the generator 11 by a switch means 21. In detail, the piezo-electric transducer 18 has an annular configuration and is provided for the emission of shockwaves. The piezo-electric transducer 19 is constructed with a disc-shaped and is provided for the emission of continuous sound or acoustical waves which may be either continuous or for a intermittent period and is preferably arranged in the opening in the annular piezo-electric transducer 18.

The switches 20 and 21 can be actuated independent of one another. Therefore, three operating modes are possible. Emission of shock waves from the piezo-electric transducer 18 and the generator 10 is possible, when the switch 20 is closed and the switch 21 is open. The emission of continuous sound with the piezo-electric transducer 19 and generator 11 will occur with the switch 21 being closed and the switch 20 being opened. Simultaneous emission of continuous sound waves and shockwaves with the piezo-electric transducers 18 and 19 and generators 10 and 15 is possible, when switches 20 and 21 are closed. This operating mode is shown in FIG. 2.

A switch 22 is also provided, and this allows the two piezo-electric transducers 18 and 19 to be switched to be parallel to one another. It is then possible to operate both piezo-electric transducers 18 and 19 in common and connect them to one of the two generators 10 or 11, dependent on whether the switches 20 and 22 are closed, with the switch 21 being opened or vice versa, with the switch 20 being open, and the switches 21 and 22 being closed.

Although various minor modifications may be suggested by those versed in the art, it should be understood that I wish to embody within the scope of the patent granted hereon all such modifications as reasonably and properly come within the scope of my contribution to the art.

I claim:

1. A device for generating focused, acoustical waves for treating life forms, said device comprising an electrically drivable acoustical wave means for generating acoustical waves for treating a life form, means for focusing the acoustical waves generated by the acoustical wave means, and an electrical generator means for driving the acoustical wave means, the generator means comprising two separate generator means with one of the two generator means producing an electrical signal for driving the acoustical wave means to generate shock waves for treating the life form and the other of the two generator means producing an electrical signal for driving the acoustical wave means to generate a periodic acoustical wave for treating the life form and the device further comprising switch means for connecting at least one of the two generator means to the acoustical wave means.

2. A device according to claim 1, wherein said acoustical wave means comprises at least one piezo-electric transducer.

3. A device according to claim 2, further including control means for operating the other generator means to create intermittent periods of electrical signal to create intermittent pulses of periodic acoustical waves.

4. A device according to claim 1, further including control means for operating the other generator means for producing a pulsed AC-signal for driving the acoustical wave means to generate a pulsed periodical acoustical wave.

5. A device according to claim 1, wherein said acoustical wave means includes a single transducer and said switch means includes a single switch for alternately connecting said single transducer to the two generator means.

6. A device according to claim 1, wherein the acoustical wave means comprises two acoustical transducers, and said switch means includes a switch for each transducer so that the two transducers can be connected independently and simultaneously to their respective generator means.

7. A device according to claim 1, wherein the acoustical wave means comprises a first acoustical transducer and a second acoustical transducer, said switch means including a first switch connected to the one generator means and having a first line extending to the first transducer, a second switch being connected to the other generator means and being connected by a second line to the second transducer and a third switch interconnecting said first and second lines so that each of the first and second transducers can be independently driven by a respective generator means and either one of the two generator means can drive both transducer.

8. A device according to claim 1, wherein the acoustical wave means comprises a first transducer and a second transducer, said first transducer being an annular transducer surrounding the second transducer, said means for focusing being positioned relative to the first and second transducers to focus acoustical waves generated by the first and second transducers to the same focal point.

9. A device for generating focused, acoustical waves for treating life forms, said device comprising an electrical drivable acoustical wave means for generating acoustical waves for treating a life form, means for focusing the acoustical waves generated by the acoustical wave means, and an electrical generator means for driving the acoustical wave means, the generator means comprising two separate generator means with one of the two generator means producing an electrical signal of high-voltage pulses for driving the acoustical wave means to generate shock waves for treating a life form and the other of the two generator means producing an electrical signal of a periodic AC-voltage for driving the acoustical wave means to generate a periodic acoustical wave for treating the life form and the device further comprising switch means for connecting at least one of the two generator means to the acoustical wave means.

10. A device according to claim 9, wherein said acoustical wave means comprises at least one piezoelectric transducer.

11. A device according to claim 9, which includes control means for operating the other generator means to create intermittent pulses of the periodic AC-voltage.

12. A device according to claim 9, wherein the acoustical wave means includes a single transducer and said switch means includes a single switch for alternately connecting said single transducer to a selected one of the two generator means.

13. A device according to claim 9, wherein the acoustical wave means comprises a first acoustical transducer and a second acoustical transducer.

14. A device according to claim 13, wherein the switch means includes a switch for each of the first and second transducers so that the two transducers can be connected independently and simultaneously to their respective generator means.

15. A device according to claim 13, wherein the switch means includes three switches arranged so that each of the first and second transducers can be connected separately to their respective generator means and both of the transducers can be selectively connected to the same generator means.

16. A device according to claim 13, wherein the first transducer is an annular transducer surrounding the second transducer and said means for focusing is arranged for focusing the acoustical waves from both the first and second transducers to the same focal point.

* * * * *